United States Patent
Ward (10) Patent No.: US 10,242,557 B2
(45) Date of Patent: Mar. 26, 2019

(54) USER-RESPONSIVE MEDICAL TRAUMA TREATMENT DEVICE

(71) Applicant: Erik Ward, Spring Grove, IL (US)

(72) Inventor: Erik Ward, Spring Grove, IL (US)

( * ) Notice: Subject to any disclaimer, the term of this patent is extended or adjusted under 35 U.S.C. 154(b) by 0 days.

(21) Appl. No.: 15/628,170

(22) Filed: Jun. 20, 2017

(65) Prior Publication Data

US 2018/0365971 A1    Dec. 20, 2018

(51) Int. Cl.
| | |
|---|---|
| G08B 13/14 | (2006.01) |
| G08B 27/00 | (2006.01) |
| G08B 21/02 | (2006.01) |
| G08B 25/10 | (2006.01) |

(52) U.S. Cl.
CPC ....... *G08B 27/001* (2013.01); *G08B 21/0277* (2013.01); *G08B 25/10* (2013.01)

(58) Field of Classification Search
CPC .............................. G08B 21/00; G08B 27/001
USPC ......... 340/568.1, 572.2, 572.4, 572.7, 572.8, 340/10.2
See application file for complete search history.

(56) References Cited

U.S. PATENT DOCUMENTS

| | | |
|---|---|---|
| 6,327,576 B1 | 12/2001 | Ogasawara |
| 6,362,778 B2 * | 3/2002 | Neher ................... G01S 5/0018 342/357.75 |
| 7,020,520 B2 | 3/2006 | Olson et al. |
| 7,123,989 B2 | 10/2006 | Pinney et al. |
| 8,565,871 B2 | 10/2013 | Tuysserkani |
| 8,762,469 B2 | 6/2014 | Lindahl |
| 8,898,568 B2 | 11/2014 | Bull et al. |
| 9,008,767 B2 | 4/2015 | Bowers |
| 9,495,962 B2 | 11/2016 | Govrin et al. |
| 9,513,370 B2 | 12/2016 | Cristache |
| 9,514,276 B2 | 12/2016 | Daynes et al. |
| 2004/0019258 A1 | 1/2004 | Kavounas et al. |
| 2006/0149322 A1* | 7/2006 | Merry ....................... A61N 1/39 607/5 |
| 2006/0226988 A1 | 10/2006 | Ernst et al. |
| 2008/0316045 A1* | 12/2008 | Sriharto ................. G06Q 50/22 340/10.1 |
| 2009/0267772 A1* | 10/2009 | Dehnadi .............. A61G 12/001 340/572.8 |
| 2013/0296719 A1* | 11/2013 | Packer ................. A61B 5/0205 600/484 |
| 2014/0004814 A1 | 1/2014 | Elghazzawi |

(Continued)

FOREIGN PATENT DOCUMENTS

WO    WO 2016/102439    6/2016

OTHER PUBLICATIONS

European Patent Office acting as International Searching Authority, Form PCT/ISA/206 and Annex to Form PCT/ISA/206 Communication Relating to the Results of the Partial International Search, dated Sep. 17, 2018, in co-pending application No. PCT/US2018/038290 (14 pages).

*Primary Examiner* — Tai T Nguyen
(74) *Attorney, Agent, or Firm* — Neal, Gerber & Eisenberg LLP (57) ABSTRACT

An improved user-responsive medical trauma treatment device system and methods are provided. The present invention makes several improvements to the emergency medical treatment industry by implementing advanced diagnostics and user-triggered feedback to more appropriately address the situation at hand.

17 Claims, 5 Drawing Sheets

(56) References Cited

U.S. PATENT DOCUMENTS

2014/0107718 A1 4/2014 Foote et al.
2016/0360336 A1* 12/2016 Gross .................... H04W 4/001

* cited by examiner

USER-RESPONSIVE MEDICAL TRAUMA TREATMENT DEVICE

BACKGROUND OF THE INVENTION

Field of the Invention

The present invention generally relates to an improved emergency medical treatment device. In particular, the present invention makes several improvements to the field of emergency medical treatment by implementing a more sophisticated user-responsive interface. Typically, emergency medical treatment systems are limited in their capacity to treat various conditions; the system and design of the current invention allows users to more effectively respond to a wider variety of trauma, which was not enabled by the prior art.

Discussion of the Prior Art

United States Patent Application No. 2011/0060378 ('378 Application), submitted by Tuysserkani, describes an automated electronic defibrillator (AED), which incorporates an internal modem to facilitate contact with emergency personnel. Depending on the embodiment, this contact may be limited to transmitting data to facilitate treatment of the party, or it may allow for communication between emergency personnel and on-scene aid-providers. Upon activation, the device would contact emergency personnel to report the incident and the need for medical assistance. The '378 Application later issued as U.S. Pat. No. 8,565,871.

United States Patent Application No. 2014/0107718 A1 ('718 Application), submitted by Foote, et al, describes an AED applied to an electronic device, such as a smart phone or MP3 player. The AED attachment would consist of two or more electrodes, an electronics module, and a means of attaching to the electronic device. The invention could be used in conjunction with the supporting electronic device to monitor the patient's condition and determine whether or not said patient is facing life-threatening harm.

U.S. Pat. No. 9,514,276 B2 ('276 Patent), submitted by Daynes, et al, describes an AED which incorporates a bump event sensor and is capable of communicating with a secondary AED unit. The first AED is also capable of incorporating and transmitting GPS information to the second AED. The AED's are able to communicate through local area network (LAN), or wirelessly, such as through Bluetooth.

U.S. Pat. No. 9,513,370 ('370 Patent), issued to Cristache, addresses the use of Radio Frequency Identification (RFID) technology to track and locate items and devices, as well as to provide status updates. RFID tags are placed on the movable items, which are then monitored by RFID readers. The readers track the movement and condition of the tagged items, allowing for remote updates. Such updates can provide not only locations, but also safety evaluations, such as whether an area is still contaminated or otherwise uninhabitable, based on the amount of time which has elapsed since removal of the RFID tagged item. User-defined updates and semantics form the basis for such determinations.

United States Patent Application No. 2006/0226988 A1 ('988 Application), submitted by Ernst, et al, describes the use of RFID technology in hotel minibars, to account for inventory and sales. By affixing RFID tags to the containers within the minibar, the movement of the product could be monitored, to account for purchases made, while not penalizing guests for products they did not purchase, if they replace them before removing them from the target area. Once the tag leaves the target area, the RFID reader will register a missing item, triggering a replacement order.

U.S. Pat. No. 6,327,576 B1 ('576 Patent), issued to Ogasawara, utilizes electronic tagging to identify when a product reaches its expiration date or passes its freshness date. Tags are coded to reflect the individual characteristics of each product, allowing a computer system to track when a given product has expired or otherwise exceeded its "use by date," thus allowing for easier removal of problem goods. Once a tagged product is received, it would create an electronic receipt, which would allow the system to automatically track expirations. Moreover, users would be able to manually scan the tags to determine whether a particular good was still within its useful period.

SUMMARY OF THE INVENTION

One of the difficulties of emergency medical treatment systems is enabling persons with little or no medical training to operate them safely and effectively, particularly during high-stress situations. While some such devices exist, they are limited in their functionality. AED's, for example, are the probably the most well-known of emergency medical treatment systems, given their prominence in public venues, and the relative ease of operation. However, they do not address the full range of conditions that may require emergency medical treatment; they are limited only to instances where the cardiac rhythm has been disrupted and the patient's heart needs to be restarted. They do provide the user step-by-step directions on how to proceed, but they do not have the capability to address needs beyond restarting the patient's heart, thus providing a multipurpose first aid kit that is deployed in the field.

Thus, the current system and methods have several unique features that result in a more efficient and effective process for providing emergency medical treatment. Firstly, the system can address a broader spectrum of conditions requiring emergency medical care. Secondly, it provides a simple and efficient process which enables even those with no medical training to respond to a medical emergency. Monitoring systems allow the device to track its own contents, and those of nearby devices, to facilitate the ordering of new components and the disposal of those that have expired, and to help determine the number of affected parties and their injuries and/or conditions. The system furthermore allows for notification to emergency personnel, including police, hospital, and fire/EMT, to best respond to the situation or situations as it/they arise.

The invention allows for patients to receive emergency medical care from lay persons, which may be critical in situations where professional care cannot be obtained in time. This increases the likelihood of survival in an emergency, where the difference between life and death or permanent injury is a matter of minutes. This further decreases the risk of harm to the patient, which might be caused by an untrained Good Samaritan, who while meaning no harm, could exacerbate a serious condition. Furthermore, it allows the patient to be stabilized before emergency response personnel arrive, thus decreasing the exigency of subsequent treatment, and thus may result in less trauma to the patient later on.

Additionally, this benefits emergency personnel. The invention not only allows untrained personnel to provide medical care in an emergency situation, but also notifies emergency personnel of the nature of the emergency, the location, and the extent of harm. The devices in conjunction could relay the nature of a crisis, such as a riot or terrorist attack, to law enforcement and other emergency responders, allowing them to be better enabled to address the situation upon arrival at the scene, or upon the patient's arrival at a treatment facility. Based on the signals emitted from the device, emergency response personnel would be notified as to whether the incident requires a single device (such as a slip and fall), a department response (such as a high-rise fire), or a multiple agency cooperative (such as a terrorist attack). The devices, both individually and in connection with a network of other devices, could help inform emergency response personnel not only how severe the incident is, but also provide an estimate as to the number of persons requiring treatment based on which supplies and how many of each were used, before the first professional arrives on the scene.

To achieve these objectives, a user-responsive medical trauma treatment device is proposed.

In a first embodiment a device for treating emergency medical conditions having at least the steps of accessing a specialized device containing various supplies to treat a variety of emergency medical conditions, activating the device, following a series of prompts from the device based on the symptoms manifested by the patient, administering treatment based on the device's directives, and awaiting further instruction. Additional steps and details may preferably include: communicating with emergency personnel through the device; reporting all observations and treatment protocol to said emergency personnel, and responding to the directives of said emergency personnel.

Another preferred embodiment of the present invention contemplates an automatic transmission of activity on behalf of the device, of any or all of the following: removal from its regular location, activation, prompts provided to the user, any subsequent actions from the user as a result, and deactivation by emergency response personnel. Additional details may preferably include: location-recognition technology, such as global positioning system equipment, whereby the device could be tracked if lost, stolen, or transported away from its regular resting place; network awareness amongst devices to determine which devices require maintenance or replacement of supplies or equipment, and when such attention becomes necessary, proximity locators to other devices, to enable emergency response personnel to locate additional supplies as quickly and efficiently as possible, in the event that additional supplies become necessary; and systematic assessment of the number of potential patients and injuries/conditions, based on the components and equipment removed from each device.

Another preferred embodiment of the present invention contemplates smart technology to determine whether the removal of components was intentional or accidental. In such an instance, components removed individually would lead to recognition that medical treatment was commencing, and the nature would be determined by the components removed, the order in which they were removed, and the timing of their removal. Alternatively, if a number of components were removed in a short period of time, the device might prompt the user to identify whether the components were intentionally removed. If no response was received, the device would assume the components were accidentally dropped, lost, or stolen. If a negative response was received, the device would default to no treatment necessary. If a positive response was received, the device would default to a series of prompts, based on the components removed.

Another preferred embodiment involves an application for smart phones and other personal electronic devices, which facilitates the treatment of emergency medical needs, without the necessity of a complete device. The application would prompt and aid the user in much the same way a complete device would, with the exception of the user obtaining components from another source.

Such embodiments do not represent the full scope of the invention. Reference is made therefore to the claims herein for interpreting the full scope of the invention. Other objects of the present invention, as well as particular features, elements, and advantages thereof, will be elucidated or become apparent from, the following description and the accompanying drawing figures.

BRIEF DESCRIPTION OF THE DRAWINGS

Other features of my invention will become more evident from a consideration of the following brief descriptions of drawings.

DETAILED DESCRIPTION OF THE PREFERRED EMBODIMENTS

Referring now the drawings with more specificity, the present invention essentially provides a user-responsive medical trauma treatment device, and/or methods and systems for utilizing such a device, as well as applications for use with smart phones and other electronic devices. Using the present invention a user may be able to administer emergency medical treatment above and beyond the capability of the average non-medically-trained person armed with the devices and tools presently on the market. In addition the system can be able to account for and work with several other variables and features discussed below.

Figure 1:
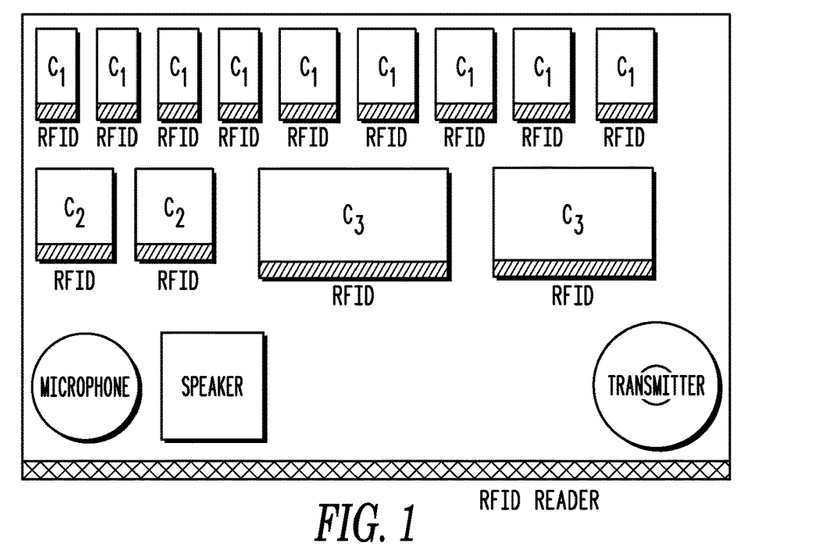
FIG. 1 is a frontal view of a representative user-responsive medical trauma treatment device.

Looking now to FIG. 1, a representative user-responsive medical trauma treatment device is shown. As shown, the device comprises various medical treatment components (C1, C2, C3), which are not limited to but may include bandages, tourniquets, wound closures, cutting implements, coagulants, and antimicrobial agents. The various medical components are tagged with a radio frequency identification (RFID) tag, or similar alternative technology. The RFID tags, or similar alternative technology, relay their position relative to the device as a whole, such that when one or more component is removed from the device, the device registers its removal and broadcasts that fact through a transmitter on, in, or adjacent to the device. This registers the removal with other connected systems, as described in greater detail in FIG. 6. This also triggers an alarm or alert to notify the user that a component has been removed (secondary alarm). The device also monitors the expiration dates and replace-by dates for components contained within the device. This information is relayed to other connected systems (such as a Satellite or command center) as described in greater detail in FIG. 6. The transmitted signal allows other users, emergency responders, and those maintaining the devices to be aware of the current inventory levels and the efficacy of the components contained therein. The signal would continue unless and until the necessary replacement occurs. The information relayed from each device to other connected systems when one or more component is removed also suggests to emergency personnel the likely injury or condition encountered, as well as the probably number of patients encountered based on the type and quantity of component(s) removed (as discussed in further detail below). The device also incorporates a speaker, allowing the user to receive commands from the device as to its proper use under a variety of conditions. This may include both general and specific prompts, depending on the nature of the prior interaction between the user and the device. Prompts may begin either once the device is activated, or after one or more components are removed from the device. These prompts will continue based on the component(s) removed. Similarly, the device incorporates a microphone, allowing the user to communicate with emergency response personnel, as well as with the unit itself.

In practice, the user would activate the device and follow the prompts provided. These prompts are varied and respond to user input. These user inputs include removal of certain components (C1, C2, C3) from the device, as well as responses to voice commands from the device. For example, the device might ask the user if the patient was bleeding. If yes, then it would direct the user to locate the source of the bleeding. If the bleeding stemmed from a gunshot wound, the device would prompt the user to remove a color-coded component, namely a powerful coagulant, to stop the blood loss. Once the component was removed, the RFID tag on the component would register with the device as missing. Upon registering the component as removed from the device, the device would then direct the user to open the package and apply the coagulant to the wound and observe to see if the bleeding had stopped. If the bleeding had stopped, the device would continue monitoring. If it had not stopped, then the device would prompt the user to another component, perhaps another package of coagulant, or if the wound was on an extremity, a tourniquet. The device could continue to ask the user if additional symptoms were visible, and respond accordingly. If the patient began suffering from seizures, the device might instruct the user to roll the patient on their side and ensure their airway was clear. The device would continue the cycle of monitoring the patient's condition and providing guidance for treatment, as described above, until emergency personnel arrive at the scene. During this exchange, the device would also be processing the quantity and nature of each component removed, converting this raw data into a more useful profile of the situation for emergency personnel. If only one package of anticoagulant was removed, the unit might determine that only one patient was suffering from an injury resulting in significant blood loss, and relay that information accordingly. It however, four packages were removed, the unit might relay that two or more individuals had suffered injury resulting in substantial blood loss, with a likelihood of a gunshot wound. Thus, emergency personnel responding to the scene would be better prepared to treat the affected parties at the scene, by having a better understanding of not only the nature of the medical emergency, but also how many potential patients they would encounter.

Figure 2:
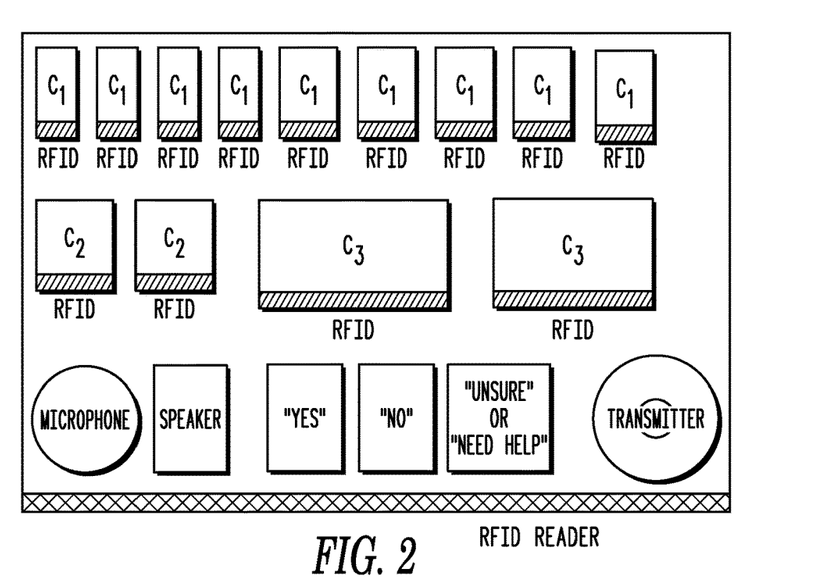
FIG. 2 is a frontal view of a representative user-responsive medical trauma treatment device incorporating analog controls in addition to purely verbal/auditory control.

Looking now to FIG. 2, an alternate embodiment of the invention is shown. The embodiment shown in FIG. 2 is similar to the embodiment described in FIG. 1, but also includes a plurality of analog command response devices, here shown as buttons. Unlike the embodiment described in FIG. 1, the embodiment in FIG. 2 allows the user to manually enter responses to prompts, even when the user is unable to utilize verbal commands, such as when background noise overrides the user's ability to register on the microphone, or when the user has speech impediments. Additionally, the embodiment shown in FIG. 2 allows the user to register an "unsure" or "need help" response, where a "yes" or "no" response would not provide an adequate response, or where the user does not feel that the prompts adequately address the situation. Triggering the "unsure" or "need help" function will put the user in contact with emergency personnel directly, who can respond to the user directly in order to address the situation and provide guidance.

Figure 3:
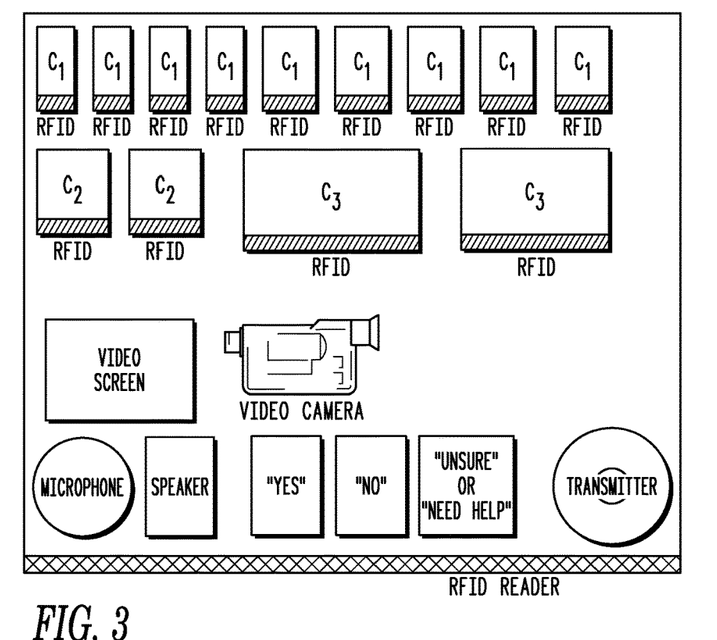
FIG. 3 is a frontal view of a representative user-responsive medical trauma treatment device incorporating analog controls in addition to purely verbal/auditory control, as well as a video input and output.

Looking now to FIG. 3, a different embodiment of the invention is shown. The embodiment depicted in FIG. 3 includes all the aspects of the embodiment depicted in FIG. 2, and includes two additional functionalities. First, the embodiment in FIG. 3 includes a video screen. The screen can be used to see depictions of what the user must do in order to properly utilize the device. These depictions may be prerecorded videos, and may include computer-generated images. These depictions may be triggered based on the user's removal of components or responses entered through the device. Second, the embodiment in FIG. 3 may include a camera, which further allows the user to communicate with emergency personnel, particularly when the user is unsure of what actions to take, as when there are multiple injuries or the source of injury is not readily apparent. The camera would allow the user to show emergency personnel the actual scene, rather than requiring the user to describe the scene to said personnel. This could also serve to provide emergency responders with information in the event the algorithm either cannot determine the nature and/or number of injuries/conditions and the number of parties, or the determination is incorrect for any reason.

Figure 4:
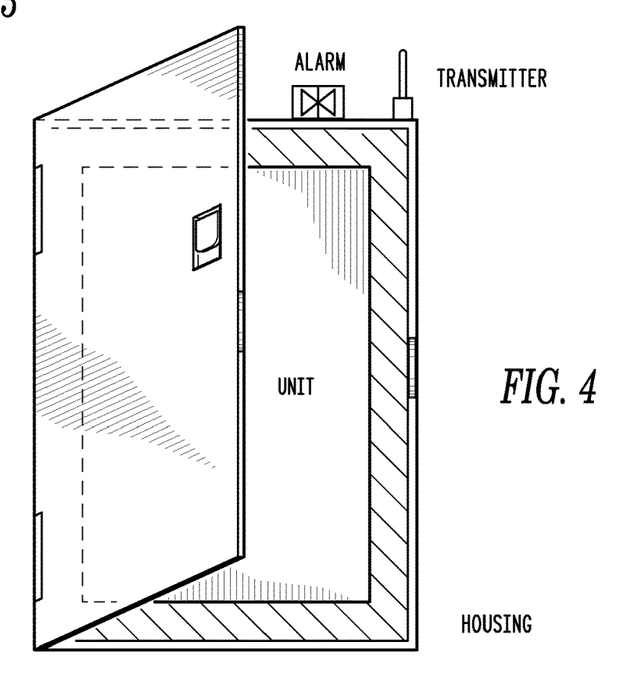
FIG. 4 is a frontal view of a representative user-responsive medical trauma treatment device contained within a closable housing, where the housing triggers an alert when opened.

Looking now to FIG. 4, a frontal view of the device is shown. Here, the device is contained within a housing, similar to the cabinets presently in use for AED's and fire extinguishers. The housing incorporates a sensor technology, such that when the housing is opened, an alert or alarm is triggered (first alarm). The alert or alarm is further broadcasted through a transmitter affixed to the housing, which reports the incident to other devices and personnel, as described in FIG. 6. When the housing is opened, the device may trigger as "activated" and begin prompting the user through its operation.

Figure 5:
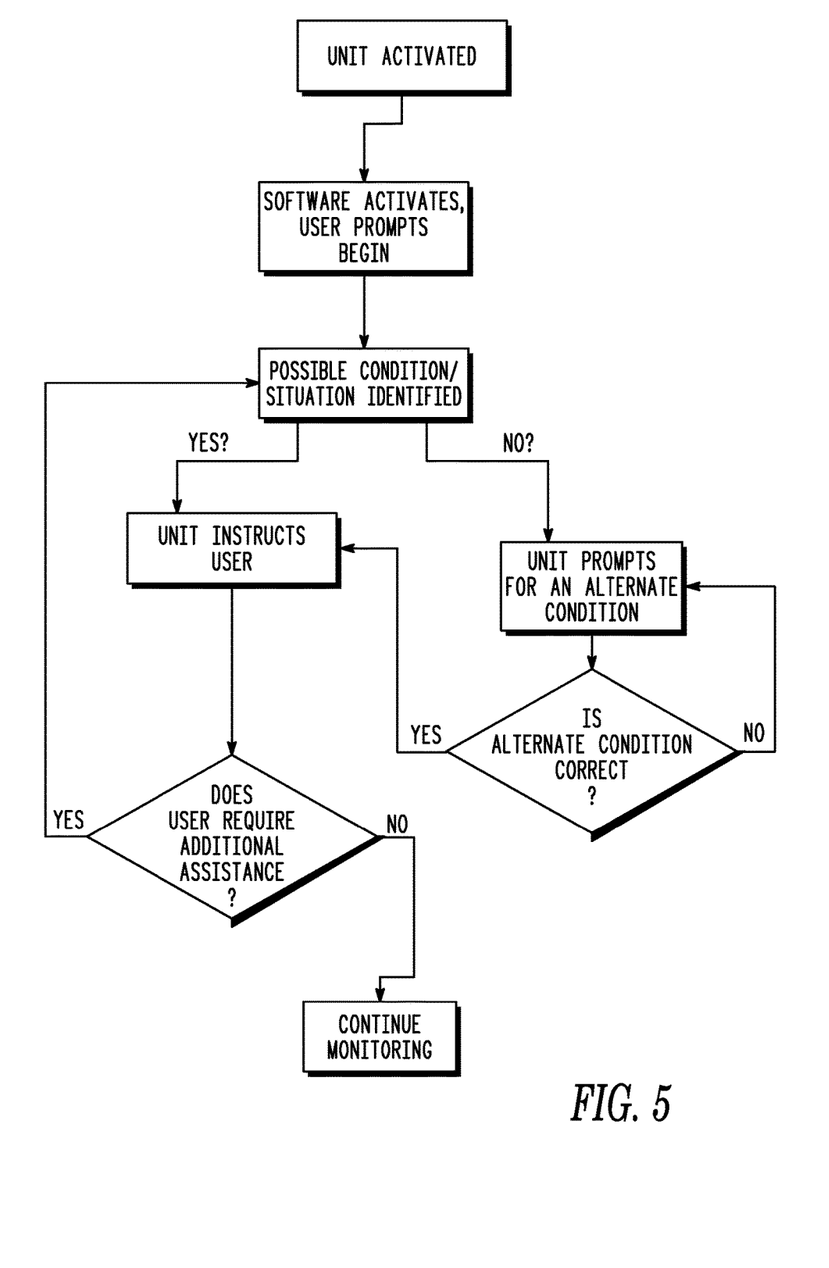
FIG. 5 is a representative flow chart describing the methods of utilizing a representative user-responsive medical trauma treatment device to provide treatment during an emergency.

Looking now to FIG. 5, a representative flow chart is shown, depicting the operation of the device through a step-by-step progression. Once the device activates, the software begins to prompt the user based on the possible nature of the incident at issue, as well as the user's input. As the user responds to the device's prompts, the device processes the responses and through the use of algorithms yields additional prompts as necessary. These prompts may be either additional instructions to the user for how to properly administer treatment, or may be additional questions for the user to answer, in order to properly diagnose the patient's condition. The device will continue to register component removals, and process the probable injuries/conditions that might require each component for treatment, and the likely number of patients based on the number of each component removed. Once the user responds that no additional assistance is necessary, the device continues to monitor the patient's condition until deactivated.

Figure 6:
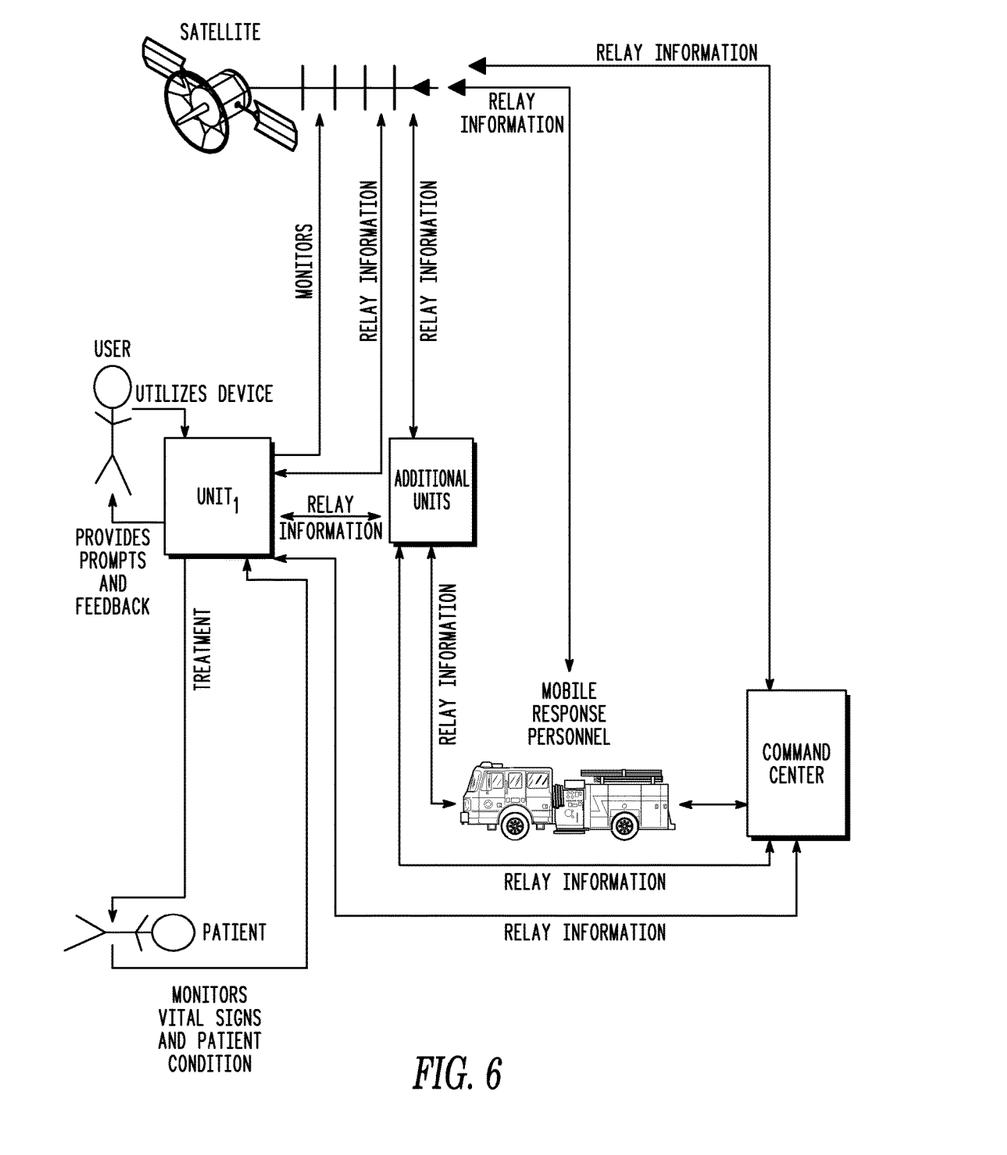
FIG. 6 is a representative diagram of how a representative user-responsive medical trauma treatment device interacts with a given user, a patient, additional devices, and other entities which may play a role in the treatment process.

Looking now to FIG. 6, a representative view of the device as part of a network is shown. The user utilizes the device to treat the patient, whose condition and vital signs are monitored by the device. The device continues provides feedback and operational prompts to the user, to facilitate its safe and effective use. Information, whether entered by the user, recorded from the patient, or determined by the device's algorithm, will be compiled and transmitted across the network. Through a network of wired or wireless connections, the device communicates with other devices, mobile response personnel, and a command center. The relays may include satellite transmission, as depicted, to provide a greater range of transmission, as well as to ensure the reliability of transmission. The relays of information allow for the user to provide the best possible treatment to the patient under the circumstances, by having the greatest access to trained personnel and the nearest location of additional supplies, should they be required. Through the network of devices and emergency personnel, users are more empowered to apply the necessary treatment, while at the same time having shorter response times from trained professionals.

Figure 7:
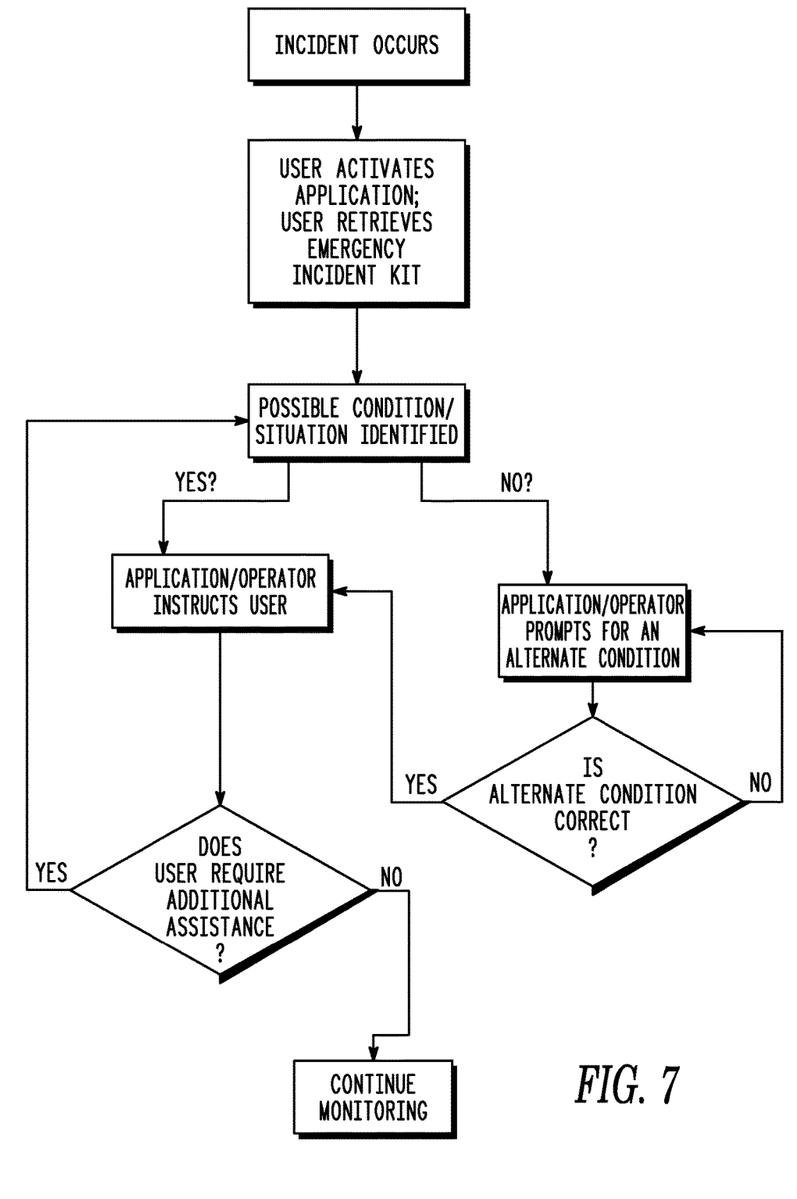
FIG. 7 is a representative flow chart describing the method of utilizing a smart phone application to administer emergency medical treatment, even without a complete device as described above.

Looking now to FIG. 7, a representative flow chart is shown, demonstrating how a user might utilize a smart phone application to diagnose and determine the appropriate means of treating a patient. Here, treatment does not require a user to have a complete device as described above, but rather enables the user to utilize their own components, which may be on hand or obtained otherwise. The method is similar to that depicted in FIG. 5, utilizing the same operative steps for treatment once activated, however it lacks the RFID or other technology for tracking components. The user is able to take direction from and interact with the device and trained personnel via their smart phone, rather than through audio-visual technology incorporated into a stand-alone device. The invention may be practiced under this embodiment as follows: some condition occurs, which requires medical assistance; a user activates an already downloaded application on their personal electronic device (smart phone, tablet, laptop computer, etc.); the user retrieves components as necessary, either from a pre-assembled kit or from various locations within the user's vicinity; the user is then either guided through a series of prompts generated by the application, or contacts a trained professional through the application, who then prompts the user, the user then follows the instructions as applicable, and when the prompts are not applicable, alternative prompts are provided; the user continues this process until such time as the treatment is no longer necessary or professional help arrives; throughout the episode, the application will continue to monitor the situation and provide data to a monitoring system and/or monitoring personnel.

Accordingly, although the invention has been described by reference to certain preferred and alternative embodiments, it is not intended that the novel arrangements be limited thereby, but that modifications thereof are intended to be included as falling within the broad scope and spirit of the foregoing disclosures and the appended drawings.

I claim:

1. A user-responsive medical trauma treatment device configured to be used by a user for a patient in need of emergency medical treatment for at least one injury, said device comprising:
   a housing;
   an apparatus within said housing;
   said apparatus containing a plurality of medical components;
   an audible sound system accessible from said apparatus;
   a transmitter, the transmitter configured to communicate with a third party system to transmit data to said third party system;
   a first proximity detector configured to detect when said apparatus is removed from said housing, wherein the audible sound system is configured to sound a first alarm in response to the first proximity detector being triggered;
   a second proximity detector associated with said apparatus, wherein the audible sound system is configured to produce sounds responsive to the second proximity detector being triggered;
   said sounds configured to prompt said user to determine where said patient's at least one injury appears to originate;
   said sounds configured to prompt said user to remove at least one of the medical components from the apparatus based on the determination of where said patient's at least one injury appears to originate; and
   said sounds configured to prompt said user to utilize the removed at least one medical component in a manner appropriate and consistent with treatment for said patient's at least one injury.

2. The device of claim 1 wherein the at least one third party system is associated with an entity selected from a group consisting of:
   a police department;
   a fire department;
   a hospital;
   an emergency medical technician;
   a doctor;
   a crisis response unit; an emergency dispatch unit;
   a nurse;
   a physician's assistant;
   an emergency management department;
   a private monitoring service; and
   a maintenance service.

3. The device of claim 1, which includes a sound receiving system accessible from said apparatus, and wherein the transmitter is configured to communicate with the third party system to transmit sound received by the sound receiving system to said third party system.

4. The device of claim 1, further configured to communicate with a second user-responsive medical trauma treatment device.

5. A user-responsive medical trauma treatment device configured to be used by a user for a patient in need of emergency medical treatment for at least one injury, said device comprising:
   a housing;
   an apparatus within said housing;
   said apparatus containing a plurality of medical components;
   an audible sound system accessible from of said apparatus;

a transmitter, the transmitter configured to communicate with a third party to transmit data to said third party system;

a primary location system configured detect if said apparatus is removed from said housing, wherein the audible sound system is configured to sound a first alarm responsive to the primary location system detecting that said apparatus has been removed from said housing; and a secondary location system configured to detect if one or more of said plurality of medical components are removed said apparatus, wherein the audible sound system is configured to produce sounds responsive to the second location system detecting that one one or more of said plurality of medical components has been removed from the apparatus;

said sounds configured to prompt said user to determine where said patient's at least one injury appears to originate;

said sounds configured to prompt said user to remove at least one medical component from the apparatus based on the determination of where said patient's at least one injury appears to originate; and said sounds configured to prompt said user to utilize the at least one medical component in a manner appropriate and consistent with treatment for said patient's at least one injury.

6. The device of claim 5, wherein
the primary location system is a radio frequency identification system.

7. The device of claim 5, wherein
the primary location system utilizes a Bluetooth communication protocol.

8. The device of claim 5, wherein the transmitter is configured to send a replenishment notice,
responsive to an occurence of a replenishment triggering condition.

9. The device of claim 5, further comprising:
all of the plurality of medical components having electronically monitored expiration dates; and
wherein when one or more of said plurality of medical components is determined to be in an expired state, the transmitter is configured to send a replacement notice.

10. The device of claim 5, further comprising:
all of the plurality of medical components having electronically monitored replacement dates; and
wherein when one or more of said plurality of medical components is determined to be nearing its replacement date, the transmitter is configured to trigger a replacement warning.

11. The device of claim 5, which includes a sound receiving system accessible from said apparatus, and wherein the transmitter is configured to communicate with the third party system to transmit sound received by the sound receiving system to said third party system.

12. The device of claim 5, further configured to use an algorithm to assess at least one probable medical condition when at least one of the plurality of medical components is removed from the apparatus.

13. The device of claim 12, further comprising: said algorithm configured to calculate a probable quantity of patients based upon the at least one probable medical condition and a quantity of each of the medical components removed from the apparatus.

14. The device of claim 5, further configured to receive data from
a monitoring third party having access to determine whether any of the plurality of medical components has been removed from the apparatus; said data associated with a location of a second device.

15. The device of claim 14 wherein:
said monitoring third party having access to results generated by an algorithm;
the algorithm configured to assess at least one probable medical condition when at least one of the plurality of medical components is removed from the apparatus, and
said algorithm configured to calculate a probable quantity of patients based upon the at least one probable medical condition and the quantity of each medical component removed from the apparatus.

16. The device of claim 5, further configured to communicate with a second user-responsive medical trauma treatment device.

17. A method of enabling a user to provide emergency medical treatment for a patient having an injury, said method comprising:
providing a user-responsive medical trauma treatment device, the device comprising: a housing; an apparatus within said housing, said apparatus containing a plurality of medical components; an audible sound system accessible from said apparatus; a transmitter, the transmitter configured to communicate with a third party system, to transmit data to said third party system; a primary location system configured to detect if said apparatus is removed from said housing, wherein the audible sound system is configured to sound a first alarm responsive to the primary location system detecting that said apparatus is removed from said housing; and a secondary location system configured to detect if one or more of said plurality of medical components are removed said apparatus, wherein the audible sound system is configured to produce sounds responsive to the second location system detecting that said medical components are removed from the apparatus;

(a) responsive to the user removing said apparatus from the housing; causing the audio sound system to produce the sounds to:
  (i) prompt the user to determine where said patient's injury appears to originate,
  (ii) prompt the user to remove at least one medical component from the apparatus based on the patient' injury; and
  (ii) prompt the user to utilize the removed at least one medical component in a manner appropriate and consistent with treatment for said patient's injury; and
(b) repeating (a) if necessary for the treatment of another injury of the patient.

* * * * *

UNITED STATES PATENT AND TRADEMARK OFFICE
CERTIFICATE OF CORRECTION

PATENT NO. : 10,242,557 B2
APPLICATION NO. : 15/628170
DATED : March 26, 2019
INVENTOR(S) : Erik Ward It is certified that error appears in the above-identified patent and that said Letters Patent is hereby corrected as shown below:

In the Claims

| | |
|---|---|
| Column 8, Line 36 | After "claim 1" insert -- , -- |
| Column 8, Line 36 | Before "third" delete "at least one" |
| Column 8, Line 66 | After "from" delete "of" |
| Column 9, Line 2 | After the first occurrence of "party" insert -- system -- |
| Column 9, Line 4 | After "configured" insert -- to -- |
| Column 9, Line 35 | After "notice" delete "," |
| Column 10, Line 35 | After the first occurrence of "system" delete "," |
| Column 10, Line 48 | After "housing" delete ";" |
| Column 10, Line 55 | Delete "(ii)" and insert instead -- (iii) -- |

Signed and Sealed this
Eighteenth Day of June, 2019

Andrei Iancu
*Director of the United States Patent and Trademark Office*